United States Patent [19]

Jacobsson

[11] Patent Number: 4,832,270
[45] Date of Patent: May 23, 1989

[54] YARN FEEDING DEVICE

[75] Inventor: Kurt A. G. Jacobsson, Ulricehamn, Sweden

[73] Assignee: Aktiebolaget IRO, Ulricehamn, Sweden

[21] Appl. No.: 110,702

[22] PCT Filed: Dec. 8, 1986

[86] PCT No.: PCT/EP86/00725
§ 371 Date: Jul. 30, 1987
§ 102(e) Date: Jul. 30, 1987

[87] PCT Pub. No.: WO87/03625
PCT Pub. Date: Jun. 18, 1987

[30] Foreign Application Priority Data

Dec. 6, 1985 [SE] Sweden ................................ 8505788

[51] Int. Cl.$^4$ ............................................. B65H 51/20
[52] U.S. Cl. ............................... 242/47.01; 66/132 R
[58] Field of Search ............... 242/47.01, 47.12, 47.13, 242/47; 66/132 R, 132 T; 139/452

[56] References Cited

U.S. PATENT DOCUMENTS

| 3,717,312 | 2/1973 | Rosen | 242/47.12 |
| 3,720,384 | 3/1973 | Rosen | 242/47.01 |
| 3,908,921 | 9/1975 | Jacobsson | 242/47.01 |
| 3,915,403 | 10/1975 | King | 242/47.01 |
| 3,995,786 | 12/1976 | Deniega | 242/47.01 |
| 4,044,962 | 8/1977 | Calamani et al. | 242/47.01 X |
| 4,367,773 | 1/1983 | Newcomb | 242/47.01 X |

Primary Examiner—Stanley N. Gilreath
Attorney, Agent, or Firm—Flynn, Thiel, Boutell & Tanis

[57] ABSTRACT

A yarn feeding device comprises a stationary storage drum from which the yarn can be withdrawn. The yarn feeding device can be operated at a positive feeding mode and at a non-positive feeding mode by means of a rotatable yarn guiding member arranged at the withdrawal end. The yarn guiding member comprises at least one yarn engagement element adapted for engaging the yarn when the rotational speed of the yarn spiralling around the withdrawal end of the storage drum tends to exceed the rotational speed of the yarn guiding member. The yarn engagement element comes out of engagement with the yarn when the rotational speed of the guiding member exceeds the rotational speed of the yarn spiralling around the withdrawal end of the storage drum.

13 Claims, 2 Drawing Sheets

YARN FEEDING DEVICE

FIELD OF THE INVENTION

The present invention relates to a yarn feeding device, preferably for a textile machine for the intermittent processing of yarn, which yarn feeding device comprises a stationary storage drum from which the yarn can be withdrawn over a withdrawal end of said drum. More particularly, the present invention relates to a yarn feeding device which can be used for selectively feeding the yarn to a textile machine in a positive feeding operation or a non-positive feeding operation.

BACKGROUND OF THE INVENTION

The term "positive feeding" defines a feeding condition during which the yarn feeding device determines the feeding speed of the yarn fed to a textile machine, in particular to a knitting machine. The term "non-positive feeding" is a well-known technical expression defining an operational state of the yarn feeding device under which the yarn can be freely withdrawn from the yarn feeding device at a yarn speed which is determined by the actual demand of yarn of the textile machine.

Yarn feeding devices for selectively positively feeding or non-positively feeding of yarn to a knitting machine are commonly known in the art. For example, U.S. Pat. No. 3,908,921 discloses a yarn feeding device for a knitting machine comprising a rotatable yarn storage drum onto which a yarn is wound for forming an intermediate store of yarn and from which the yarn can be unwound and fed to the knitting machine. The prior art yarn feeding device comprises a movable yarn control element which is disposed adjacent to the withdrawal path of the yarn near the withdrawal end of the storage drum. This movable yarn control element can be brought into a first position in which it defines a fixed withdrawal point of the yarn withdrawn from the storage drum so as to limit the yarn withdrawal speed to the tangential speed of the storage drum. In a second position of the movable yarn control element it does not come into contact with the unwinding yarn so that the yarn can be freely withdrawn from the storage drum at a withdrawal speed which is determined by the actual demand of yarn of working elements in the knitting machine. This prior art yarn feeding device can only be equipped with a rotating storage drum as the rotational speed of the storage drum in the first mode of operation for the positively feeding of yarn to the textile machine determines the yarn feeding speed. In the second mode of operation for the non-positively feeding of yarn to the knitting machine, the rotational speed determines the amount of yarn wound on the storage drum per time unit. Hence, the increasing or decreasing of the rotational speed of the storage drum during this second mode of operation results in an increasing or decreasing store of yarn on the drum. When changing the mode of operation from the positive feeding state to the non-positive feeding state, an abrupt adjustment of the rotational speed of the storage drum becomes necessary. The abrupt changing of the rotational speed of the rotatable storage drum causes problems due to the high inertia of the storage drum.

In view of this state of art, the present invention is based on the technical task of creating a yarn feeding device adapted for the selectively positively or non-positively feeding of yarn to a textile machine having a good dynamic behaviour.

In accordance with the present invention, the yarn feeding device is equipped with a stationary yarn storage drum, as known per se in the art (EP-A-107 110) and comprises a rotatable yarn-guiding member arranged at the withdrawal end of the storage drum. The rotatable yarn-guiding member is driving at a rotational speed which depends on the operational speed of the textile machine at least during the time intervals of the positive feeding of yarn to the textile machine. The rotatable yarn-guiding element comprises at least one yarn engagement element adapted for engaging the yarn when the rotational speed of the yarn spiralling around the withdrawal end of the storage drum tends to exceed the rotational speed of the yarn-guiding member so as to define a yarn feeding speed during these time intervals of positive feeding. The yarn engagement element is adapted for coming out of engagement with said yarn so as to allow a free withdrawal of yarn from the storage drum independent from the rotational speed of the guiding member when the rotational speed of the guiding member exceeds the rotational speed of the yarn spiralling around the withdrawal end of the storage drum.

In one embodiment, the first rotational speed is chosen such that the desired positive yarn feeding speed is obtained. The second rotational speed is chosen such that it exceeds the first rotational speed.

In a second embodiment, the rotating yarn guiding member can be continuously driven at a fixed rotational speed if the textile machine requires a yarn feeding speed under positive feeding conditions which exceeds the actual yarn demand of the textile machine under non-positive yarn feeding conditions.

BRIEF DESCRIPTION OF THE DRAWINGS

Hereinafter, preferred embodiments of the yarn feeding device in accordance with the present invention will be described with reference to the enclosed drawings, in which.

DETAILED DESCRIPTION

Figure 1:
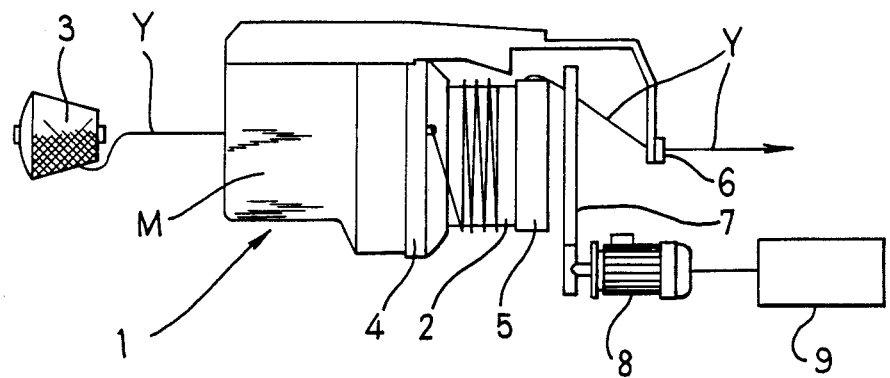
FIG. 1 is a side-view on a yarn feeding device in accordance with the present invention.

As shown in FIG. 1, a yarn feeding device 1 comprises a stationary (i.e. nonrotatable) yarn storage drum 2, onto which a yarn Y coming from a yarn spool 3 can be wound by means of a rotatable winding-on member 4 driven by a motor. The stationary storage drum 2 is equipped with a withdrawal rim 5 defining the withdrawal end of the storage drum. Yarn feeding devices of the above-described design are commonly known in the art and one example is described in the assignee's prior pre-published EP application No. 83 109 818.1 (Publication Number 107110) and corresponding U.S. Pat. No. 4 627 474.

The yarn withdrawn from the storage drum 2 passes through a guiding eyelet 6 and is fed to a textile machine, which may be a flat or circular knitting machine.

A rotatable guiding member 7 is rotatably journalled between the withdrawal end 5 of the stationary storage drum 2 and the guiding eyelet 6. The axis of rotation of the rotatable guiding member 7 coincides with that of the stationary storage drum.

The rotatable guiding member 7 is driven by an electric motor 8 which in turn is controlled by a control unit 9.

The rotatable yarn guiding member 7 is driven by the electric motor 8 at a rotational speed, which depends on the operational speed of the knitting machine at least during those time intervals when a positive feeding of yarn should take place.

Figure 2:
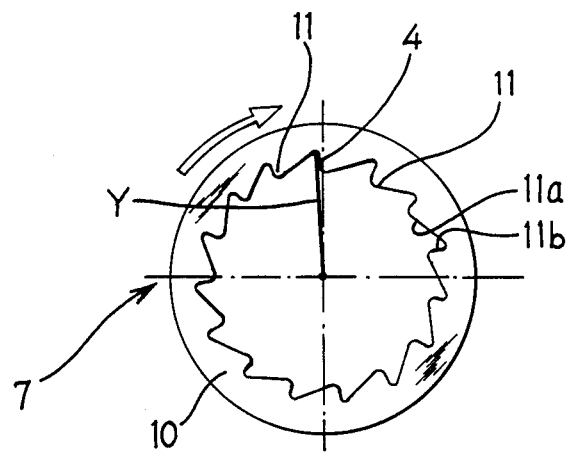
FIG. 2 is a representation of a first embodiment of the rotatable yarn guiding member.

As shown at FIG. 2, the rotatable guiding member 7 preferably has the form of a ring 10 having thereon an inner circular yarn guiding surface, and also having a plurality of inwardly-directed teeth 11 which project from this guiding surface and have front faces 11a which are inclined with respect to the radial direction opposite to the direction of the rotational movement of the guiding member 7. The direction of rotational movement is indicated by an arrow.

The rear faces 11b of the directed teeth 11 of said guiding member 7 are adapted for engaging the yarn Y when the rotational speed of the yarn spiralling around the withdrawal end 5 of the storage drum 2 tends to exceed the rotational speed of the guiding member 7. In other words, the direction of inclination of the teeth 11 with respect to the radial direction is chosen such that the yarn Y is caught during its withdrawal from the storage drum 2 when the rotational speed of the contact point or withdrawal point of the yarn at the withdrawal rim 5 tends to exceed the rotational speed of said rotatable guiding member 7. In this case, the rotational speed of the guiding member 7 limits the yarn withdrawal speed so that positive feeding takes place.

In those periods of time of a knitting cycle when the yarn is to be withdrawn from the storage drum at a speed corresponding to the actual demand of yarn of the textile machine, the guiding member 7 is rotated faster than the rotational speed of the withdrawal point of the yarn with regard to the storage drum 2 so that the yarn Y is no longer caught by the teeth 11, but freely slides over the inclined front faces 11a of the teeth so that the yarn can be freely withdrawn from the storage drum in a non-positive feeding condition.

Preferably, the teeth 11 have rounded tips.

In other words, the rotatable guiding member 7 of the yarn feeding device 1 in accordance with the present invention allows a free withdrawal of the yarn from the storage drum as long as the rotational speed of the guiding member 7 exceeds that of the contact point or withdrawal point of the yarn at the withdrawal rim 5 of the storage drum.

When reducing the rotational speed of the rotating guiding member 7 below the rotational speed of the contact point of the yarn at the withdrawal rim, then the yarn Y is caught by the teeth so that the feeding takes place at a positive feeding speed which is defined by the rotational speed of the rotating guiding member 7.

Due to the small inertia or mass of the ring-formed guiding member 7, the rotational speed thereof can be changed quickly. Hence, the positive feeding speed can be changed very quickly.

In flat knitting machines the yarn consumption ceases during the change of the direction of movement of the carriage. When applying the yarn feeding device in accordance with the present invention to flat knitting machines, the rotational speed of the guiding member 7 does not have to be reduced to zero, since the speed of the yarn is automatically adapted to the new yarn demand because the yarn comes out of engagement with the teeth 11 as soon as the yarn demand of the knitting machine falls below a certain threshold.

If it is desired to terminate a positive feeding operation and to allow a withdrawal of yarn in accordance with the demand of the knitting machine, it is only necessary to increase the rotational speed of the guiding member 7 so that the yarn Y is no longer caught by the teeth 11 but is only riding on the rounded tips of the teeth 11 of the ring 10 forming the guiding member 7.

The yarn feeding device in accordance with the present invention can be applied to a first type of knitting machine where the yarn consumption during the non-positive feeding condition is above the yarn consumption during the positive feeding condition as well as to a second type of knitting machine where the yarn consumption in a non-positive feeding condition is below the positive feeding speed. In the first case, the yarn guiding member 7 is driven during the time intervals of positive feeding of yarn at a first rotational speed depending on the speed of operation of the knitting machine, while for non-positive feeding the rotating guiding member 7 is driven at a second rotational speed exceeding the first rotational speed. The second rotational speed must be chosen to be high enough that it is above the rotational speed of the withdrawal point of the yarn at the maximum yarn demand of the textile machine during the non-positive condition.

In the second case, the yarn guiding member 7 can be continuously driven at a rotational speed corresponding to the rotational speed of the textile machine. As soon as the actual yarn demand of the textile machine falls below the positive feeding speed, the yarn comes out of engagement with the guiding member 7 so that the non-positive feeding takes place.

Figure 3:
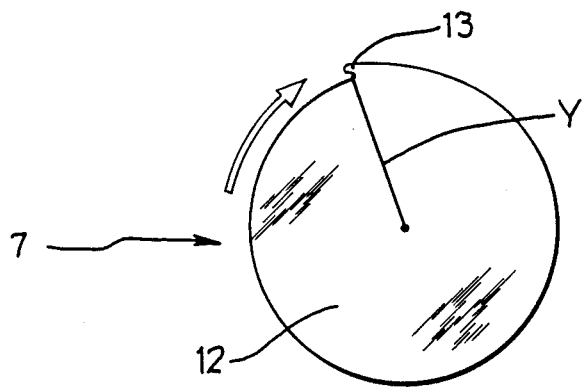
FIG. 3 is a representation of a second embodiment of the yarn guiding member.
Figure 4:
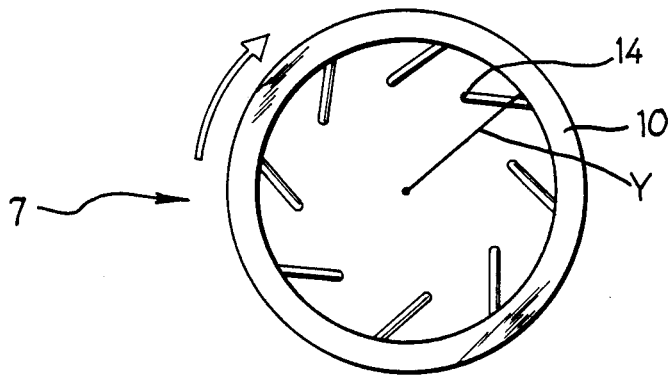
FIG. 4 is a third embodiment of a yarn guilding member.
Figure 5:
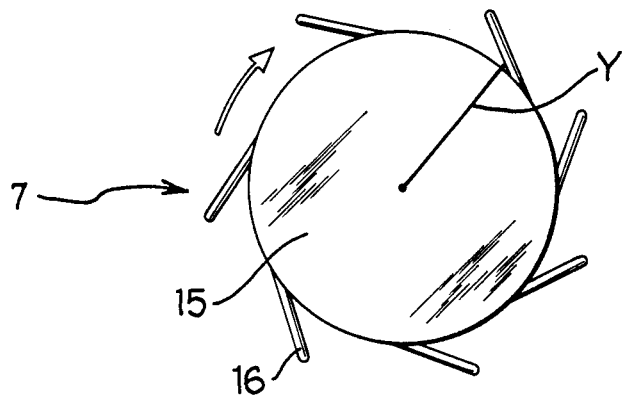
FIG. 5 is a fourth embodiment of the yarn guiding member.

Alternative embodiments of the guiding member 7 are shown at FIGS. 3 to 5.

As shown at FIG. 3, the rotatable guiding member 7 can have the form of a disc 12 having a single tooth 13 extending in the radial outward direction, which tooth is inclined with respect to the radial direction opposite to the direction of rotation of the guiding member 7.

Alternatively, the guiding member 7 may have the form as shown at FIG. 4. This embodiment of the rotating guiding member 7 comprises a ring 10 which is equipped with a plurality of inwardly-directed pins 14, which are also inclined with respect to the radial direction opposite to the direction of rotational movement.

Another embodiment as shown at FIG. 5 comprises a rotatable disc 15 which is equipped with a plurality of outwardly-directed pins 16 which are inclined with respect to the radial direction of the disc 15 opposite to the direction of rotational movement of the guiding member 7.

I claim:

1. A yarn feeding device for selective positive or non-positive feeding of yarn to a yarn consuming textile machine, said device comprising:
    a non-rotatable storage drum having a central axis, a peripheral storage surface and a withdrawal end;
    a yarn winding-on member rotatably associated with said storage drum in order to form a yarn storage containing a plurality of yarn windings on said storage surface of said storage drum, said yarn being withdrawn from said storage surface over said withdrawal end at a withdrawal point which rotates around said axis with a rotational speed dependent on the yarn consumption of the textile machine;

a yarn guiding member arranged adjacent to said withdrawal end, said yarn guiding member being supported for rotation around said axis and being provided with a substantially circular guiding surface for guiding the withdrawn yarn adjacent the withdrawal point;

at least one yarn engaging element provided on said yarn guiding member and projecting over the guiding surface at least during periods of positive yarn feeding, said yarn engaging element having a front face and a rear catching-face as seen in the direction of rotation of the withdrawal point for hindering said yarn to pass the yarn engagement element during rotation of the withdrawal point; and driving means connected with the winding-on member to rotatively drive the winding-on member relative to the drum;

the improvement comprising:

a variable-speed drive means separate from the driving means of the winding-on member and connected with said yarn guiding member to at least define the rotational speed of the yarn withdrawal point during positive feeding and for changing the rotational speed of the yarn withdrawal point during positive feeding; and said yarn engagement element being arranged in fixed relationship on said yarn guiding member in order to project over said guiding surface during both positive and non-positive feeding.

2. A yarn feeding device according to claim 1, wherein said variable-speed drive means increases the rotational speed of the yarn guiding member over the rotational speed of the yarn withdrawal point under positive feeding in order to move the yarn out of engagement with said rear catching-face and to terminate positive feeding.

3. A yarn feeding device according to claim 2, wherein said front face of said yarn engaging element has an inclination with respect to the radial direction from said axis which is opposite to the direction of rotation of the yarn withdrawal point in order to allow the yarn to slide over the yarn engagement element as soon as the rotational speed of the yarn guiding member exceeds the rotational speed of the yarn withdrawal point after termination of positive feeding.

4. A yarn feeding device according to claim 1, wherein the front face of said yarn engaging element has an inclination with respect to the radial direction from said axis which is opposite to the direction of rotation of the yarn withdrawal point in order to allow the yarn to slide over said yarn engaging element as soon as the rotational speed of the yarn withdrawal point falls below the rotation speed of the yarn guiding member for starting non-positive feeding of yarn.

5. A yarn feeding device according to claim 1, wherein said yarn guiding member is formed as a ring having a radially inner surface which defines said circular guiding surface and having at least one projection which projects radially inwardly from said guiding surface, said projection defining thereon said front face, said front face as it projects radially inwardly also being sloped or inclined opposite to the direction of rotation of the yarn withdrawal point.

6. A yarn feeding device according to claim 5, wherein said yarn guiding member has a plurality of said projections formed thereon and projecting radially inwardly from said guiding surface in substantially uniformly angularly spaced relationship therearound.

7. A yarn feeding device according to claim 1, wherein said yarn guiding member has a radially outer surface defining said circular guiding surface and having at least one radially-outwardly extending projection defining said yarn engaging element, said projection defining said front face thereon with said front face being sloped or inclined opposite to the direction of rotation of the yarn withdrawal point as the projection projects radially outwardly.

8. A yarn feeding device according to claim 2, wherein said drive means rotatably drives said yarn guiding member during positive feeding at a first rotational speed in synchronism with the operational speed of the textile machine, and wherein said drive means rotatably drives said yarn guiding member during non-positive feeding at a second rotational speed exceeding said first rotational speed.

9. A yarn feeding device for selective positive or non-positive feeding of yarn to a yarn consuming textile machine, said device comprising:

a non-rotatable storage drum having a central axis, a peripheral storage surface and a withdrawal end;

a yarn winding-on member rotatably associated with said storage drum in order to form a yarn storage containing a plurality of yarn windings on said storage surface of said storage drum, said yarn being withdrawn from said storage surface over said withdrawal end at a withdrawal point which rotates around said axis with a rotational speed dependent on the yarn consumption of the textile machine;

a yarn guiding member arranged adjacent to said withdrawal end, said yarn guiding member being supported for rotation around said axis and being provided with a substantially circular guiding surface for guiding the withdrawn yarn adjacent the withdrawal point;

at least one yarn engaging element provided on said yarn guiding member and projecting over the guiding surface at least during periods of positive yarn feeding, said yarn engaging element having a front face and a rear catching-face as seen in the direction of rotation of the withdrawal point for hindering said yarn to pass the yarn engagement element during rotation of the withdrawal point; and drive means connected with the winding-on member and the yarn guiding member respectively, in order to at least define the rotational speed of the yarn withdrawal point during positive feeding;

the improvement comprising:

said front face of said yarn engaging element having an inclination with respect to the radial direction to said axis opposite to the direction of rotation of the yarn withdrawal point in order to allow the yarn to slide over said yarn engaging element as soon as the rotational speed of the yarn withdrawal point falls below the rotational speed of the yarn guiding member for starting non-positive yarn feed.

10. A yarn feeding device according to claim 9, wherein said yarn engaging element is arranged in fixed relationship on said yarn guiding member in order to project over said guiding surface during both positive and non-positive feeding.

11. A yarn feeding device according to claim 10, wherein said yarn guiding member is continuously driven during both positive and non-positive feeding at a rotational speed in synchronism with the operational speed of the textile machine.

12. A yarn feeding device according to claim 9, wherein the drive means includes a variable speed drive connected to the yarn guiding member for driving the yarn guiding member separate from the winding-on member.

13. A yarn feeding device for selective positive or non-positive feeding of yarns to a yarn consuming textile machine, said device comprising:

- a non-rotatable yarn storage drum having a central longitudinally-extending axis, a surrounding peripheral storage surface, and a withdrawal end;
- a yarn winding-on member disposed adjacent said storage drum and supported for rotation about said central axis for winding yarn onto said peripheral storage surface to form a yarn storage thereon containing a plurality of yarn windings, said yarn being withdrawal from said storage surface over said withdrawal end at a withdrawal point which orbits around said axis at a rotational speed dependent on the yarn consumption of the textile machine;
- a yarn guiding member arranged adjacent to the withdrawal end of said storage drum and being supported for rotation about said axis, said yarn guiding member defining thereon a substantially circular guiding surface which surrounds said axis and guides the withdrawn yarn adjacent the withdrawal point;
- at least one yarn engaging element fixedly provided on said yarn guiding member and projecting radially outwardly from the guiding surface so as to be disposed in the path of the withdrawal yarn as the withdrawal point rotates during both positive and non-positive feeding, said yarn engaging element having a front face and a rear yarn-catching face as seen in the direction of rotation of the withdrawal point, said front face permitting the withdrawal yarn to pass in one direction over the yarn engaging element while the rear yarn-catching face restricts the yarn from passing over the yarn engaging element in the opposite direction; and
- variable-speed drive means for rotatably driving the yarn guiding member separate from the winding-on member to at least define the rotational speed of the yarn withdrawal point during positive feeding and for also permitting non-positive feeding of yarn without requiring any rethreading of the yarn, said drive means causing the yarn guiding member to be driven at a rotational speed which exceeds the rotation of the withdrawal point during non-positive feeding.

* * * * *